United States Patent [19]

Rogers et al.

[11] Patent Number: 5,697,968
[45] Date of Patent: Dec. 16, 1997

[54] CHECK VALVE FOR INTRALUMINAL GRAFT

[75] Inventors: Russell L. Rogers, Munith; Rodney E. Turk, West Bloomfield, both of Mich.

[73] Assignee: Aeroquip Corporation, Maumee, Ohio

[21] Appl. No.: 513,337

[22] Filed: Aug. 10, 1995

[51] Int. Cl.⁶ ..................................................... A61F 2/06
[52] U.S. Cl. .................. 623/1; 623/12; 606/194; 137/614.04
[58] Field of Search .................. 623/1, 12; 606/192, 606/194, 195; 251/149.6, 251; 137/614.03, 614.04

[56] References Cited

U.S. PATENT DOCUMENTS

| | | | |
|---|---|---|---|
| 2,451,218 | 10/1948 | Hengst | 137/614.04 |
| 2,864,628 | 12/1958 | Edleson | 137/614.04 |
| 4,195,623 | 4/1980 | Zeff et al. | |
| 4,195,637 | 4/1980 | Gruntzig et al. | |
| 4,271,839 | 6/1981 | Fogarty et al. | |
| 4,354,523 | 10/1982 | Hochmuth et al. | 251/149.6 |
| 4,386,601 | 6/1983 | Trick | |
| 4,508,112 | 4/1985 | Seeler | |
| 4,509,554 | 4/1985 | Failla | 137/614.04 |
| 4,577,631 | 3/1986 | Kreamer | |
| 4,649,914 | 3/1987 | Kowalewski | |
| 4,733,665 | 3/1988 | Palmaz | |
| 4,739,762 | 4/1988 | Palmaz | |
| 4,740,207 | 4/1988 | Kreamer | |
| 4,762,130 | 8/1988 | Fogarty et al. | |
| 4,769,029 | 9/1988 | Patel | |
| 4,774,949 | 10/1988 | Fogarty | |
| 4,776,337 | 10/1988 | Palmaz | |
| 4,787,899 | 11/1988 | Lazarus | |
| 4,793,348 | 12/1988 | Palmaz | |
| 4,795,458 | 1/1989 | Regan | |
| 4,877,025 | 10/1989 | Hanson | |
| 4,955,895 | 9/1990 | Sugiyama et al. | |
| 5,048,510 | 9/1991 | Hauschild et al. | 623/11 |
| 5,102,417 | 4/1992 | Palmaz | |
| 5,156,620 | 10/1992 | Pigott | |
| 5,192,311 | 3/1993 | King et al. | |
| 5,330,528 | 7/1994 | Lazim | |
| 5,534,024 | 7/1996 | Rogers et al. | 623/12 |

OTHER PUBLICATIONS

"Design of an Inflatable Endovascular Aortic Prosthesis", JP Pigott, HG Beebe, Jobst Vascular Center, Toledo, Ohio, 1 page.

Primary Examiner—John G. Weiss
Assistant Examiner—Bruce E. Snow
Attorney, Agent, or Firm—Emch, Schaffer, Schaub & Porcello, Co., L.P.A.

[57] ABSTRACT

An intraluminal graft assembly is provided with a double ball check valve which is normally urged to a closed position by a single compression spring acting on a first ball to urge it into sealing engagement with a valve seat. A spacer between the first ball and the second ball urges the second ball into sealing engagement with a second valve seat when the first valve is in sealing engagement with its associated valve seat. A threaded coupler engages and displaces the second valve axially out of engagement with its associated valve seat carrying with it the spacer and first ball thereby displacing also the first ball out of engagement with its associated valve seat. The double ball check valve permits the introduction of fluid into and removal of fluid from the cavity defined by inner and outer wall members of an intraluminal graft member.

7 Claims, 3 Drawing Sheets

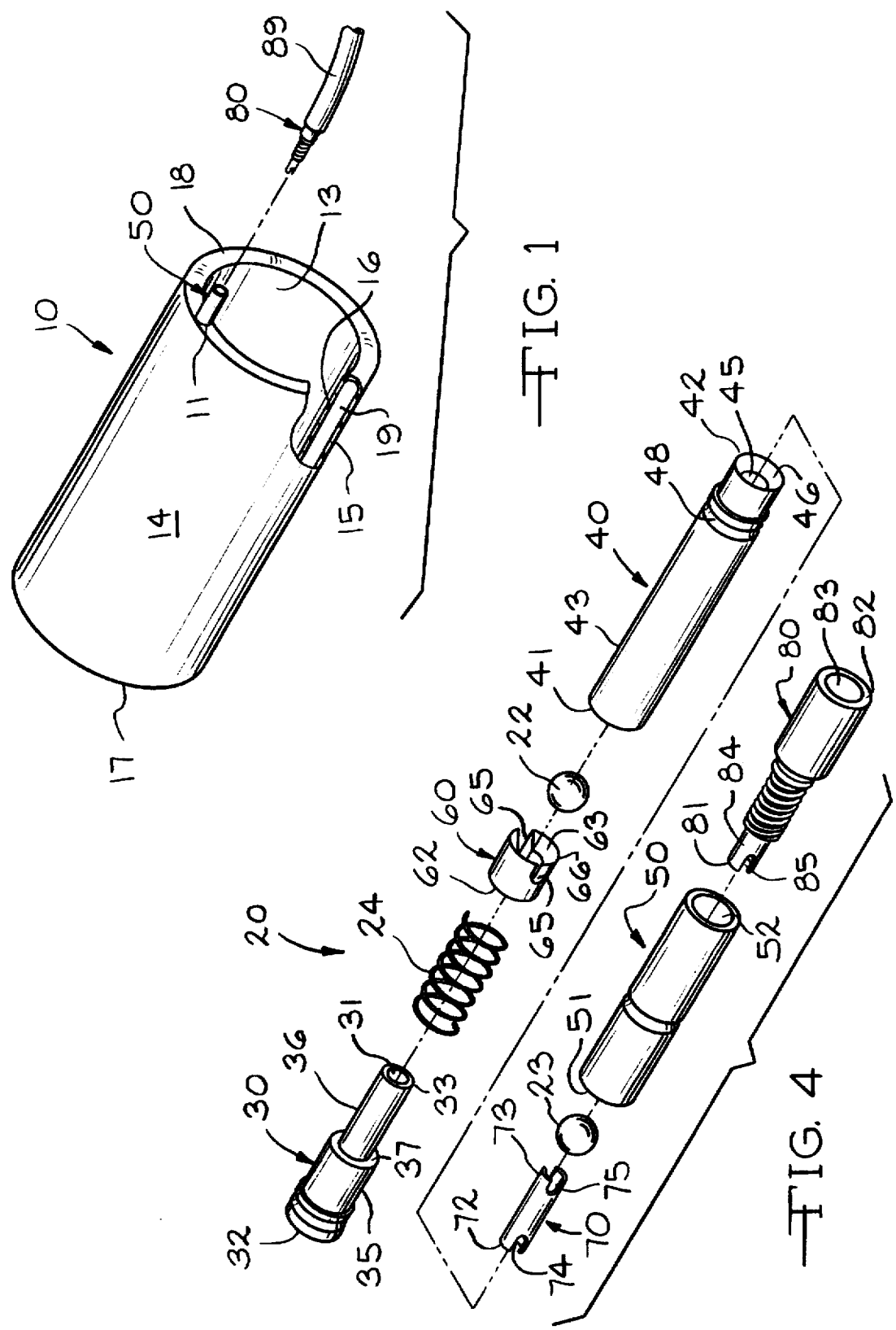

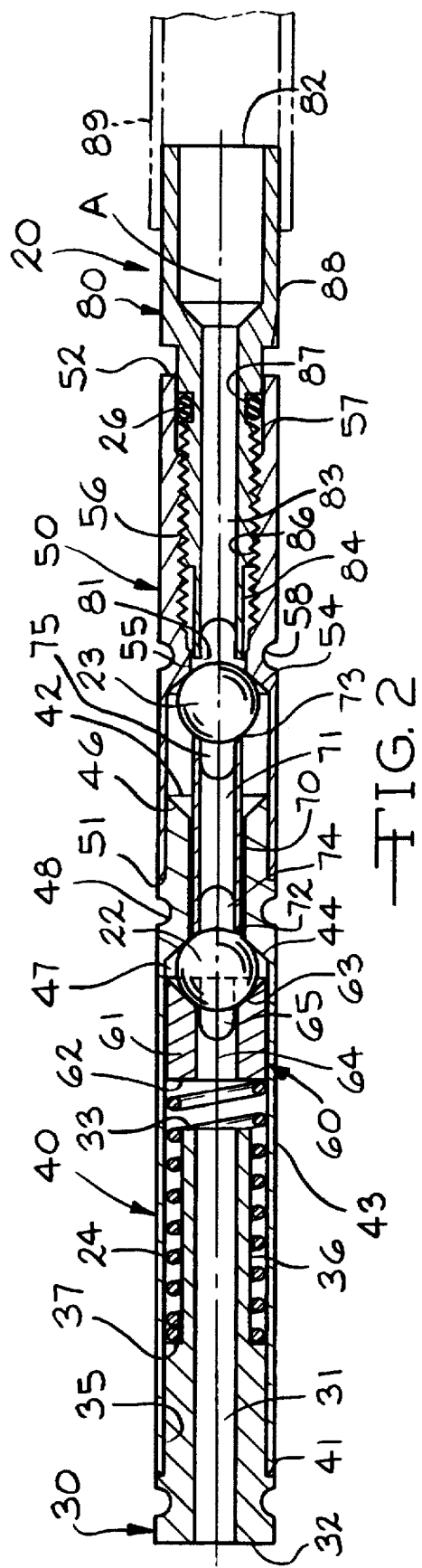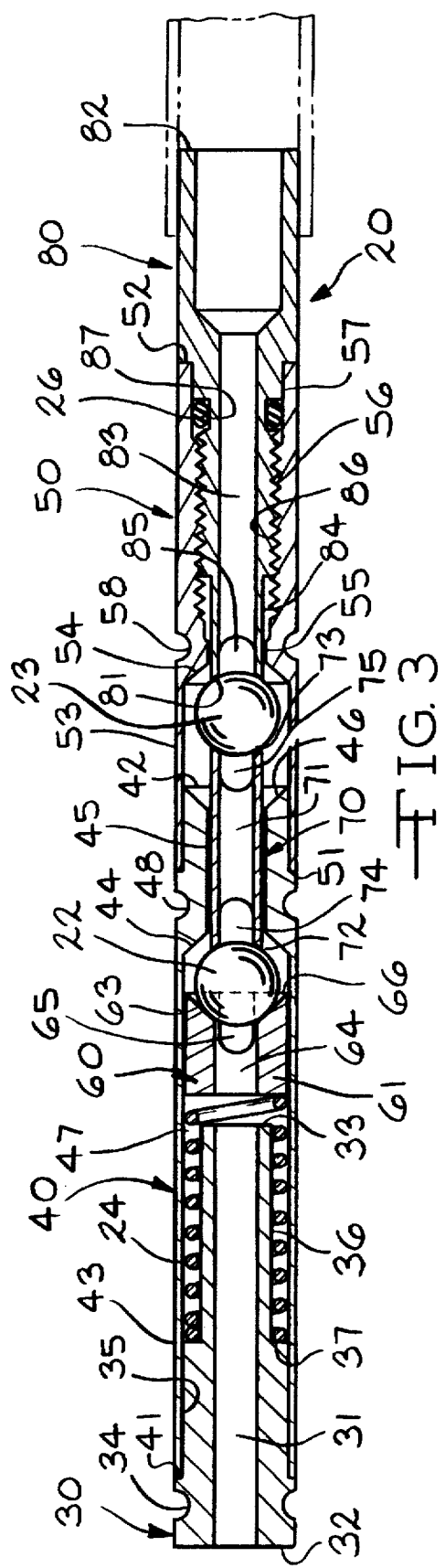

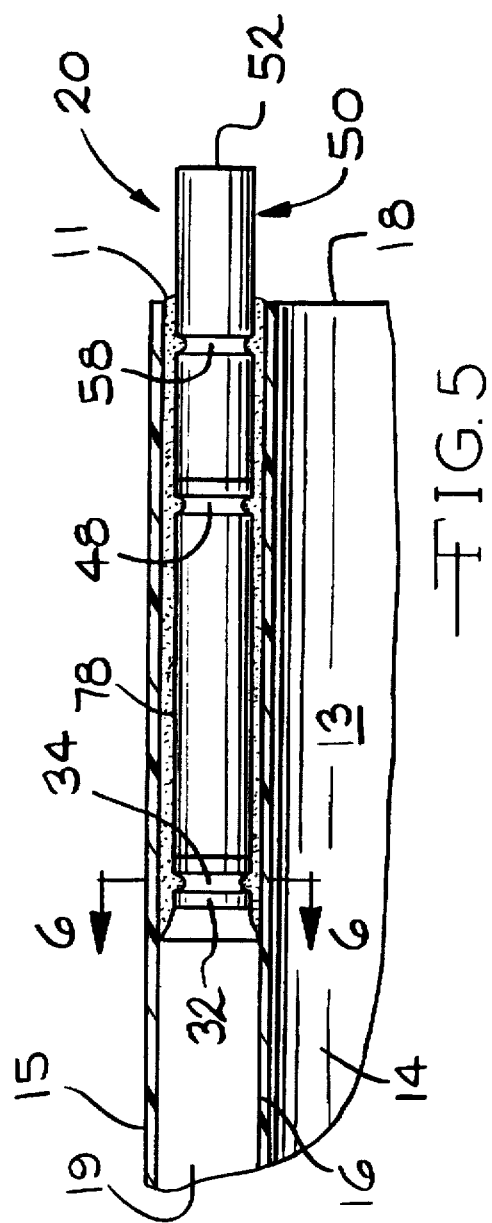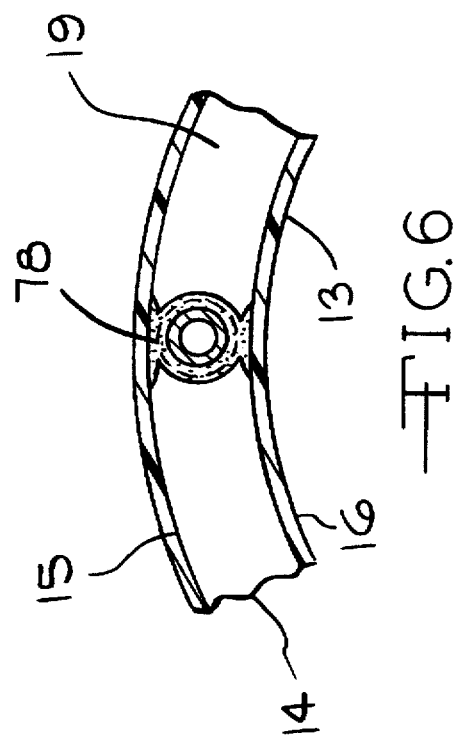

CHECK VALVE FOR INTRALUMINAL GRAFT

BACKGROUND OF THE INVENTION

The present invention relates an intraluminal graft assembly and more specifically a dual-ball check valve for the graft member of such assembly. The check valve provides means for conveying fluid into the space or cavity defined by the spaced apart walls and ends of the graft member to facilitate proper positioning and placement of the intraluminal graft assembly in the blood vessel of a patient.

The use of the stents and grafts in repairing diseased or damaged blood vessels is well know and is particularly beneficial in repairing the aortic aneurysms. As a result of miniaturization of the grafts and stents, it has been possible to implant such grafts and stents without invasive surgery which requires opening of the abdominal and/or chest cavity for repair of the aorta or other blood vessels in that area.

Treatment of aneurysms through non-invasive procedures is well known in the art and is disclosed in the following prior art patents: U.S. Pat. Nos. 4,740,207, 5,156,620, 4,577, 631, 4,776,337, 4,787,899 and 5,330,528.

The graft prosthesis may consist of a double-walled cylinder made of extruded polytetrafluoroethylene (ePTFE) or other suitable biocompatible material, and sealed at the ends creating a closed space between the inner and outer walls and the opposing ends and an open lumen for blood flow defined by the inner surface of the inner wall. The graft prosthesis is collapsed during the insertion and implantation procedure. Thus, the collapsed graft prosthesis will be inserted in a remote vessel such as the femoral artery and directed to the desired repair site, for example the aorta, by means of a catheter. Upon reaching the site of the damaged vessel to be repaired, fluid such as air or a saline solution is introduced into the cavity defined by the inner and outer walls joined at their opposite ends to expand the graft prosthesis to a position such that the exterior surface of the outer wall adjacent the opposing ends contacts and becomes sealingly engaged to the inner surface of the blood vessel.

SUMMARY OF THE INVENTION

The present invention includes a dual-ball check valve for an intraluminal graft prosthesis which permits the introduction of fluids from a remote location outside of a patient's body into the cavity of a graft which has been positioned in a blood vessel such as the aorta, remote from the site of entry into the body for example, the femoral artery. After the introduction of fluid such as saline solution into the cavity, the surgeon will make a determination of whether the graft has been properly positioned in the precise location for optimal benefit to the patient. The intraluminal graft assembly of the present invention permits the surgeon, if he determines that a slight repositioning of the graft is necessary or desirable, to remove a sufficient amount of the saline solution or other fluid from the cavity to permit appropriate repositioning of the graft prosthesis assembly. In addition, the valve effectively prevents leakage of such fluid following final positioning and implantation of the graft in the blood vessel.

Accordingly, it is an object of the present invention to provide a graft assembly having suitable valve means for introduction of fluid into the cavity defined by the graft member and for removal and reintroduction of such fluid as necessary during the implantation procedure, and which will provide a leak-proof seal following a final positioning and implantation of the graft assembly.

The intraluminal graft assembly prosthesis of the present invention comprises a dual-ball check valve secured to the graft member for retention therewith following implantation in the blood vessel. The graft member, formed of a suitable bio-compatible material, has inner and outer walls joined together at their respective adjoining ends to form a cavity when the graft member is in the expanded condition. The dual-ball check valve is of sufficiently small size to permit introduction of the graft assembly prosthesis into the patient through a remote blood vessel and includes a plurality of body members joined together with two of the body members having valve seats each of which is contoured to be sealingly engaged by a ball. A spring yieldingly urges one ball, preferably formed of rubber, into sealing engagement with its associated valve seat of the first body member. A spacer is positioned between the balls and is of a length such as to cause the second ball, preferably formed of stainless steel, to sealingly engage its associated valve seat of the second body member when the first ball is sealingly engaged to its valve seat of the first body member. The second body member of the check valve has an internally threaded portion which extends out of the graft member.

A threaded coupler has an extension portion which engages the second ball upon being threadedly engaged to the second body member. Continued threading of such coupler inwardly and the axial movement resulting therefrom causes the extension portion to engage and then displace the second ball away from and out of engagement with the valve seat of the second body member. Such movement of the second ball is transmitted to the first ball by means of a spacer thereby moving such first ball out of engagement with its associated valve seat and opening the check valve for the introduction of fluid into or removal of fluid from the cavity of the graft member.

The present invention also provides a method for implanting an intraluminal graft assembly which permits positioning of the graft member at a remote site to be repaired, the introduction of fluid into the cavity of the graft member, the subsequent removal of fluid from such cavity, repositioning of the graft member and final introduction of fluid into such cavity.

BRIEF DESCRIPTION OF THE DRAWINGS

FIG. 1 is a perspective view of the intraluminal graft assembly of the present invention with the check valve extending from the graft member and with a coupler shown disconnected from the check valve.

FIG. 2 is a sectional view of the check valve with the coupler partially engaged thereto and with the balls in the sealed position.

FIG. 3 is a view similar to FIG. 2 with the coupler threaded to its maximum full engagement causing displacement of the balls axially away from their respective valve seats thereby opening the check valve.

FIG. 4 is an exploded perspective view showing the various elements of the check valve and coupler.

FIG. 5 is a fragmentary view, partially in section, showing the check valve secured to the inner and outer walls of the graft member.

FIG. 6 is a sectional view taken through line 6—6 of FIG. 5.

DESCRIPTION OF THE INVENTION

Referring to the drawings, there is shown an intraluminal graft assembly 10 for use with a threaded coupler member 80 for introducing saline solution or other fluid into the graft assembly 10. The graft assembly 10 includes a graft member 14 and a check valve generally designated manufactured of a suitable bio-compatible material well known in the art, such as for example, extruded polytetrafluoroethylene (ePTFE) and includes an outer cylindrical wall 15 and an inner cylindrical wall 16 joined at opposing ends 17 and 18. The outer wall 15 has a larger diameter than the inner wall 16 such that when the respective outer wall 15 and inner wall 16 are at their maximum sizes, they, along with the ends 17 and 18 define a cavity 19. As will be described in greater detail, the check valve 20 is permanently secured in the cavity 19 by adhesive or other suitable means joining it to the outer wall 15 and the inner wall 16.

The graft member 14 may be collapsed to a size permitting it and the check valve 20 secured thereto to be introduced into a remote blood vessel and moved through such blood vessel to the aorta or other damaged vessel intended to be repaired with the intraluminal graft assembly. Upon positioning at the site of the blood vessel to be repaired, fluid may be introduced into the cavity 19 through the valve 20 from the coupler 80 and hose 89 associated therewith to expand the graft member 14 to its full size shown in FIG. 1. When so expanded to its full size, the outer wall 15 in the areas adjacent the respective ends 17 and 18 will engage and be secured to the wall of the blood vessel being repaired with the central portion of the graft member 14 between such ends 17 and 18 spanning the damaged or diseased portion of the blood vessel. When the graft member 14 is thus expanded, the innermost surface 13 of the inner wall 16 defines an open lumen for the flow of blood.

Referring now to FIGS. 2 through 4, the check valve includes a spring guide member 30 joined to a first or rear body member 40 which in turns is joined to a second or outer body member 50. The joined body members 30, 40 and 50, extend along an axis A and, when opened, define passageways for the flow of fluid therethrough.

The spring guide member 30 extends from an inner end 32 to an outer end 33 and has a central passageway 31 extending therethrough. The spring guide member 30 is provided with an outwardly facing annular groove 34 intended to receive a suitable adhesive for affixing to the outer wall 15 and inner wall 16 of graft member 14. The spring guide member 30 is provided with a cylindrical wall portion 35 of a predetermined diameter on the opposite side of the groove 34 from the inner end 32 and a reduced size cylindrical wall portion 36 defining a spring guide between the cylindrical wall portion 35 and the outer end 33. The cylindrical wall portion 35 is joined to the reduced size cylindrical wall portion by a shoulder 37.

The first or rear body member 40 extends from an inner end 41 to an outer end 42 and includes an extremely thin wall section 43 extending from the inner end 41 to an area having an inwardly tapering conical surface defining a valve seat 44. A passageway 45 extends along the axis A from the valve seat 44 to the outer end 42. If desired, the outer end 42 may be provided with a lead-in surface 46 tapering inwardly toward the axis and toward the inner end 41.

The inner surface of that portion of the thin walled section 43 in the area adjacent the inner end 41 is sealingly adhered to the cylindrical wall portion 35 of the spring guide member 30. The first body member 40 thus cooperates with the spring guide member 30 to define a cavity 47 in which is positioned a compression spring 24, a pusher 60 and a first ball 22. The first ball 22 is sized for sealing engagement with the valve seat 44 and, thus, significantly larger in diameter than the passageway 45. The first ball 22 is preferably made of rubber such as Fluorel obtained from 3M Company and has a Durometer of 75 to 80 Shore A to provide an effective seal with the valve seat 44 capable of sealing water at 10 psig. It is within the contemplation of the invention, however, that the first ball could be stainless steel or other metal suitable for implantation in the human body. The pusher is located on the opposite side of the first ball 22 from the valve seat 44. The pusher 60 has a cylindrical wall 61 with an outer surface sized to be slidingly received in the cavity 47 in close engagement with the inner surface of the thin walled section 43. The pusher 60 extends from an inner end 62 to an outer end 66 having an outwardly tapering wall portion defining a ball seat 63. A central passageway 64 extends from the inner end 62 to the ball seat 63. The cylindrical wall 61 is provided with one or more slots 65 which permit fluid to flow therethrough even though the ball 22 is engaged to the ball seat 63.

A compression spring 24 encircles the reduced cylindrical portion 36 of the spring guide member 30 and has one end engaging the shoulder 37 between the cylindrical wall portion 35 and reduced cylindrical wall 36. The spring 24 extends beyond the outer end 33 of the spring guide member 30 and engages the inner end 62 of the pusher 60. Thus, the compression spring 24 yielding urges the pusher 60 to a position causing the first ball 22 to be sealingly engaged to the valve seat 44.

The first body member 40 is provided with outwardly facing annular groove 48 for receiving glue for adhering that portion of the check valve to the outer wall 15 and inner wall 16 of the graft member 14.

The second body member 50 extends from an inner end 51 to an outer end 52. The second body member 50 has a thin walled section 53 in the area adjacent the inner end 51, the inner surface of which is sealingly engaged to the outer surface of the first body member 40 adjacent its outer end 42.

In an area generally centrally positioned between the inner end 51 and the outer end 52, the inner surface of the second body member 50 tapers inwardly toward the axis A and toward the outer end 52 to define a valve seat 54. Preferably the valve seat 54 defines a section of a cone. In the area between the valve seat 54 and the outer end 52 is a short inwardly facing cylindrical section 55 followed by an enlarged threaded section 56. A further enlarged inwardly facing cylindrical wall section 57 extends between the threaded section 56 and the outer end 52. An outwardly facing annular groove 58 is provided in an area of the second body member 50 in the vicinity of the short inwardly facing cylindrical section 55. As can be seen in FIGS. 1 and 5, the outer end 52 and a short portion of the second body member 50 adjacent thereto extends outwardly through an aperture 11 in the end 18 of the graft member 14.

Positioned in the cavity between the valve seat 54 and the outer end 42 of the first body member 40 is a second ball 23 having a diameter larger than the diameter of the short inwardly facing cylindrical section 55 and sized to become sealingly engaged with the valve seat 54. Preferably, the second ball is formed of stainless steel or other suitable metal; however, it could be formed of rubber similar to that of the first ball.

Positioned in the space between the first ball 22 and second ball 23 is a spacer 70 having an axial passageway 71. The spacer 70 extends from an inner end 72 abutting the first ball 22 to an outer end 73 abutting the second ball 23 and has a length such that when the first ball 22 is in sealing engagement with the valve seat 44 of the center body member 40, the second ball 23 will be in sealing engagement with the valve seat 54 of the outer member 50. The spacer 70 is provided with one or more slots 74 extending through the side wall and extending inwardly from the inner end 72 and one or more of the slots 75 extending through the side wall and extending to the outer end 73. As a result of the slots 74 and 75, engagement of the balls 22 and 23 with the respective inner end 72 and outer end 73 does not create a seal. Thus, the passageway 71 is always open to the flow of fluid between the slots 74 and 75. As a result, when the first ball 22 is disengaged from the valve seat 44 of the first body member 40 and the second ball 23 is disengaged from the valve seat 54 of the second body member 50, fluid may flow through the slots 75, passageway 71 and the slots 74 and on through the space between the first ball 22 and valve seat 44 of the center body 40, through the slots 65 of the pusher 60, through its passageway 64, through the passageway 31 of the spring guide member 30, and into the cavity 19 of the graft member 14.

The intraluminal graft assembly 10 thus far described is intended to be positioned in and remain permanently in a damaged blood vessel. As such all members must be manufactured of a biocompatible material such as a stainless steel (304) or a suitable plastic.

In order to expand the intraluminal graft assembly 10 from its collapsed or folded condition required for movement through the veins and positioning at the damaged site to its expanded condition forming cavity 19, there is provided a coupler 80 which extends from an inner end 81 to an outer end 82. The coupler has a passageway 83 extending from the inner end 81 to the outer end 82 and an extension portion 84 having an exterior cylindrical wall adjacent the inner end 81 sized to be received in the short inwardly facing cylindrical section 55 of the second body member 50. One or more slots 85 is formed in the extension portion 84 and extends from the inner end 81 toward the outer end 82. As a result of the slots 85, there will be no sealing engagement between the coupler 80 and its extension 84 when the inner end 81 engages the second ball 23.

The coupler 80 is also provided with a threaded section 86 for engagement with the threaded section 56 of the second body member 50 and an annular groove 87 in which is positioned an annular sealing ring 26 for providing a fluid tight seal when the coupler 80 is engaged to the second body member 50. If desired, the coupler 80 may be provided with an enlarged shoulder 88 sized to engage the outer end 52 of the second body member 50 to limit the extent to which the coupler 80 may extend into the second body member 50.

As can be readily seen from comparing FIGS. 2 and 3, when the inner end 81 of the coupler 80 is disengaged or Out of contact with the second ball 23, the second ball 23 will be sealingly engaged with the valve seat 54 of the second body member 50 and the first ball 22 will be in sealing engagement with the valve seat 44 of the first body member 40. Rotation of the coupler 80 in a direction further inwardly causes the inner end 81 to move the second ball 23 axially thereby displacing it out of engagement with the valve seat 54. Such movement of the second ball 23 moves the spacer 70 axially in the same direction which, in turn, moves the first ball 22 axially out of engagement with valve seat 44 carrying with it the pusher 60 against the yielding pressure exerted by spring 24. This is the position shown in FIG. 3 which shows the valve 20 in the fully open position, thereby permitting fluid to flow through the passageway 83 and slots 85 of the coupler 80, through the gap between the second ball 23 and the valve seat 54, through the slots 75, passageway 71 and slots 74 of the spacer 70, through the space between the first ball 22 and the valve seat 44, through the slots 65 and passageway 64 of pusher 60 and through the passageway 31 and into the cavity 19 of the graft member 14. When the valve 20 is in the open position of FIG. 3, fluid may also be removed from the cavity 19 simply by applying a negative pressure at the outer end 82 of the coupler 80 through the hose 89.

Referring now to FIGS. 5 and 6, it may be seen how the check valve 20 is retained in the graft member 14, only a fragment of which is shown. As previously described, the check valve 20 extends through an aperture 11 in the end 18 and extends into the cavity 19 defined by the gap between the outer wall 15, inner wall 16 and ends 17 and 18 of the graft member 14. An appropriate adhesive 78 is applied throughout the length of the valve 20 and to the adjacent portions of the surfaces of the outer wall 15 and inner wall 16 facing the cavity 19. Although the thickness is shown in FIGS. 5 and 6 for illustration purposes as fairly thick, in reality it is applied as a very thin film except in the areas of the grooves 34, 48 and 58 where it desirably fills such grooves. A suitable adhesive is a heat activated adhesive sold under the brand name of Chemlok by Lord Corporation, 2000 West Grandview Blvd., Erie, Pa. After the check valve 20 is properly positioned in the graft member 14 as shown in FIGS. 5 and 6, the adhesive 78 may be subjected to heat thereby activating the adhesive and causing it to firmly secure the check valve 20 to the graft member 14.

Many modifications will become apparent to those skilled in the art. Accordingly, the scope of the present invention should be measured only by the scope of the claims appended hereto.

We claim:

1. An intraluminal graft assembly comprising:
    (a) a graft member formed of a biocompatible material capable of being in a folded collapsed condition and in a non-folded expanded condition, said graft member having inner and outer tubes joined together, said inner and outer tubes, when in an expanded condition, defining an annular chamber; and
    (b) a check valve having a first portion including an opening positioned in and communicating with said chamber and secured to said graft member and a second portion including an end extending outwardly from said chamber, said check valve having
        (i) a passageway extending between said first portion opening and said second portion end;
        (ii) first and second valve seats in said passageway;
        (iii) first and second balls positioned for movement, respectively, between (A) sealing engagement with said first and second valve seats and (B) disengagement therefrom;
        (iv) a spring yieldingly urging said first ball into engagement with said first valve seat;
        (v) a pusher between said spring and said first ball;
        (vi) a spacer extending through said first valve seat and a portion of said passageway urging said second ball into sealing engagement with said second valve seat; and
    (c) a coupler engageable with said check valve, said coupler having a probe engageable with said second ball to urge said second ball against the yielding urging of said spring to disengage said second ball from said second valve seat.

2. A graft assembly according to claim 1, wherein said check valve is provided with threads in the vicinity of said second end and said coupler is provided with a threaded portion mating with said threads.

3. An intraluminal graft assembly for positioning in a blood vessel comprising:
   (a) an intraluminal graft member having inner and outer layers of flexible material each defining an annular cross-sectional configuration cooperating when expanded to define a chamber, said inner layer having a first side defining an interior wall of said chamber and a second side defining a passageway for the flow of fluid; and
   (b) a check valve secured to said graft member providing access to said chamber, said check valve including:
      (i) an inner body member having an exterior wall, an outlet end, an inlet end and a passageway extending along an axis from said inlet end to said outlet end, said outlet end communicating with said chamber, said exterior wall having a first portion adjacent said inlet end with a relatively small size and a second portion with a larger size and cooperating therewith to define a shoulder;
      (ii) a central body member extending from an inlet end to an outlet end joined to said inner body member second portion and cooperating therewith to define a cavity, said central body member having an entrance passageway extending from said inlet end, said passageway having an outwardly flaring portion defining a valve seat spaced from said inlet end and defining a portion of said cavity;
      (iii) a first ball having a diameter larger than the size of said entrance passageway positioned in said cavity for axial movement from an open position spaced from said valve seat to a closed position engaged to said valve seat;
      (iv) a spring having one end engaged to said inner body member shoulder yieldingly urging said first ball toward said closed position;
      (v) an outer body member extending from a first end engaged to said central body member to a second end and having a threaded portion in the vicinity of said second end, an axial passageway extending from said first end to said second end and having an outwarding flaring portion defining a second valve seat between said first end and said second end;
      (vi) a second ball movable axially from a closed position in sealing engagement with said second valve seat to an open position spaced from said second valve seat; and
      (vii) a spacer extending axially extending between said first ball and said second ball, the length of said spacer being such as to urge said second ball into sealing engagement with said second valve seat when said spring urges said first ball into sealing engagement with said first valve seat;
   (c) a threaded coupler engageable with said outer body member threaded portion, said threaded coupler having an extension portion engageable with said second ball upon threaded engagement of said coupler with said threaded portion, continued threading of said coupler to said outer body member after initial engagement of said extension portion with said second ball displacing said second ball to its open position and said first ball to its open position.

4. An intraluminal graft assembly for positioning in a blood vessel comprising:
   (a) an intraluminal graft member having inner and outer layers of flexible material each defining an annular cross-sectional configuration cooperating when expanded to define a chamber, said inner layer having a first side defining an interior wall of said chamber and a second side defining a passageway for the flow of fluid; and
   (b) a check valve secured to said graft member providing access to said chamber, said check valve including:
      (i) an inner body member having an exterior wall, an outlet end, an inlet end and a passageway extending along an axis from said inlet end to said outlet end, said outlet end communicating with said chamber, said exterior wall having a first portion adjacent said inlet end with a relatively small size and a second portion with a larger size and cooperating therewith to define a shoulder;
      (ii) a central body member extending from an inlet end to an outlet end joined to said inner body member second portion and cooperating therewith to define a cavity, said central body member having an entrance passageway extending from said inlet end, said passageway having an outwardly flaring portion defining a valve seat spaced from said inlet end and defining a portion of said cavity;
      (iii) a first ball having a diameter larger than the size of said entrance passageway positioned in said cavity for axial movement from an open position spaced from said valve seat to a closed position engaged to said valve seat;
      (iv) a spring having one end engaged to said inner body member shoulder yieldingly urging said first ball toward said closed position;
      (v) a pusher positioned between said spring and said first ball;
      (vi) an outer body member extending from a first end engaged to said central body member to a second end and having a threaded portion in the vicinity of said second end, an axial passageway extending from said first end to said second end and having an outwarding flaring portion defining a second valve seat between said first end and said second end;
      (vii) a second ball movable axially from a closed position in sealing engagement with said second valve seat to an open position spaced from said second valve seat; and
      (viii) a spacer extending axially extending between said first ball and said second ball, the length of said spacer being such as to urge said second ball into sealing engagement with said second valve seat when said spring urges said first ball into sealing engagement with said first valve seat;
   (c) a threaded coupler engageable with said outer body member threaded portion, said threaded coupler having an extension portion engageable with said second ball upon threaded engagement of said coupler with said threaded portion, continued threading of said coupler to said outer body member after initial engagement of said extension portion with said second ball displacing said second ball to its open position and said first ball to its open position.

5. An intraluminal graft assembly comprising:
   (a) an intraluminal graft member having inner and outer layers of flexible material each defining an annular cross-sectional configuration cooperating when expanded to define a chamber, said inner layer having a first side defining an interior wall of said chamber and a second side defining a passageway for the flow of fluid;
   (b) a check valve secured to said graft member and having an opening providing access to said chamber, said check valve including:

(i) a housing having a first end portion connected to said intraluminal graft and a second end and a passageway extending from said first end portion to said second end and communicating with said opening;

(ii) a first enlarged area in said passageway defining a first shoulder facing away from said second end;

(iii) a second enlarged area in said passageway defining a second shoulder closer to said second end than said first shoulder and facing away from said second end;

(iv) a first ball movable in said first enlarged area from a position sealingly engaging said first shoulder to a position spaced therefrom;

(v) a second ball movable in said second enlarged area from a position sealingly engaging said second shoulder to a position spaced therefrom;

(vi) a spring yieldingly urging said first ball into sealing engagement with said first shoulder;

(vii) a pusher between said spring and said first ball;

(viii) a spacer positioned in said passageway between said first ball and said second ball, said spacer having a length causing said second ball to be urged into sealing engagement with said second shoulder when said first ball is in sealing engagement with said first shoulder; and (ix) connection means adjacent said second end; and (c) a coupler fastenable with said connection means and including a probe positionable in said passageway at said second end, said probe being engageable with second ball to urge said second ball away from said second shoulder upon said coupler being fastened to said connection meads.

6. An intraluminal graft assembly according to claim 5, wherein said connection means includes threads and said coupler includes mating threads, rotation of said coupler relative to said check valve causing said probe to engage said second ball and further rotation of said coupler causing said probe to displace said ball out of engagement with said second shoulder.

7. An intraluminal graft assembly according to claim 5, wherein said coupler has a passageway extending therethrough.

* * * * *